United States Patent
Dacquay et al.

(10) Patent No.: US 7,381,917 B2
(45) Date of Patent: Jun. 3, 2008

(54) FOOTSWITCH ASSEMBLY WITH POSITION MEMORY

(75) Inventors: Bruno Dacquay, Irvine, CA (US); Victor B. Mezhinsky, Brea, CA (US)

(73) Assignee: Alcon, Inc., Hunenberg (CH)

( * ) Notice: Subject to any disclaimer, the term of this patent is extended or adjusted under 35 U.S.C. 154(b) by 132 days.

(21) Appl. No.: 11/524,364

(22) Filed: Sep. 20, 2006

(65) Prior Publication Data

US 2008/0067046 A1  Mar. 20, 2008

(51) Int. Cl.
*H01H 3/14* (2006.01)
(52) U.S. Cl. ........................... 200/86.5; 74/512
(58) Field of Classification Search ............... 200/86.5; 307/112, 119, 124; 73/146; 606/1, 166, 606/167, 169; 74/512, 560, 561; 318/551; 604/65; 433/101
See application file for complete search history.

(56) References Cited

U.S. PATENT DOCUMENTS

| | | |
|---|---|---|
| 3,930,431 A | 1/1976 | Magadini |
| 4,168,707 A | 9/1979 | Douvas et al. |
| 4,267,414 A | 5/1981 | Brueggeman |
| 4,274,411 A | 6/1981 | Dotson, Jr. |
| 4,383,167 A | 5/1983 | Gmeinder et al. |
| 4,652,215 A | 3/1987 | Kuroyanagi et al. |
| 4,837,857 A | 6/1989 | Scheller et al. |
| 4,901,454 A | 2/1990 | Walkhoff |
| 4,965,417 A | 10/1990 | Massie |
| 4,983,901 A | 1/1991 | Lehmer |
| 5,091,656 A | 2/1992 | Gahn |
| 5,157,603 A | 10/1992 | Scheller et al. |
| 5,268,624 A | 12/1993 | Zanger |
| 5,342,293 A | 8/1994 | Zanger |
| 5,403,276 A | 4/1995 | Schechter et al. |
| 5,554,894 A | 9/1996 | Sepielli |
| 5,580,347 A | 12/1996 | Reimels |
| 5,635,777 A | 6/1997 | Telymonde et al. |
| 5,787,760 A | 8/1998 | Thorlakson |
| 5,810,765 A | 9/1998 | Oda |
| 5,910,110 A | 6/1999 | Bastable |
| 5,983,749 A | 11/1999 | Holtorf |
| 5,990,400 A | 11/1999 | Hoshino |
| 6,010,496 A | 1/2000 | Appelbaum et al. |
| 6,055,458 A | 4/2000 | Cochran et al. |

(Continued)

FOREIGN PATENT DOCUMENTS

EP    0789929    7/2002

(Continued)

OTHER PUBLICATIONS

Japanese Patent Abstract; Publication No. 2000-229102, Aug. 22, 2000.

*Primary Examiner*—Michael A Friedhofer
(74) *Attorney, Agent, or Firm*—W. David Lee

(57) ABSTRACT

A footswitch assembly with a position memory includes adjustable mounting mechanisms. A first adjustable mounting mechanism moves the heel cup portion on the treadle pedal assembly to a predetermined position to accommodate the length of a user's foot. A second adjustable mounting mechanism moves the side wing assembly to predetermined position to accommodate the width of a user's foot. A third adjustable mounting mechanism adjusts the force needed to move the treadle pedal assembly.

11 Claims, 4 Drawing Sheets

U.S. PATENT DOCUMENTS

| | | |
|---|---|---|
| 6,117,126 A | 9/2000 | Appelbaum et al. |
| 6,149,621 A | 11/2000 | Makihara |
| 6,150,623 A | 11/2000 | Chen |
| 6,179,829 B1 | 1/2001 | Bisch et al. |
| 6,360,630 B2 | 3/2002 | Holtorf |
| 6,452,120 B1 | 9/2002 | Chen |
| 6,452,123 B1 | 9/2002 | Chen |
| 6,514,268 B2 | 2/2003 | Finlay et al. |
| D478,323 S | 8/2003 | Peterson et al. |
| 6,639,332 B2 | 10/2003 | Metzler et al. |
| 6,659,998 B2 | 12/2003 | DeHoogh et al. |
| 6,674,030 B2 | 1/2004 | Chen et al. |
| 6,743,245 B2 | 6/2004 | Lobdell |
| 6,862,951 B2 | 3/2005 | Peterson et al. |
| 6,962,094 B2 * | 11/2005 | Porter et al. ............... 74/512 |
| 6,962,581 B2 | 11/2005 | Thoe |
| 7,012,203 B2 * | 3/2006 | Hanson et al. ............ 200/86.5 |
| 7,019,234 B1 * | 3/2006 | Mezhinsky et al. ........ 200/86.5 |
| 7,193,169 B2 * | 3/2007 | Mezhinsky et al. ........ 200/200 |
| 2003/0047434 A1 | 3/2003 | Hanson et al. |
| 2003/0073980 A1 | 4/2003 | Finlay et al. |
| 2003/0213333 A1 | 11/2003 | McVicar |
| 2007/0152508 A1 | 7/2007 | Mezhinsky |

FOREIGN PATENT DOCUMENTS

| | | |
|---|---|---|
| EP | 1394828 | 3/2004 |
| GB | 1063067 | 3/1967 |
| WO | WO 9613845 | 5/1996 |
| WO | WO 9808442 | 3/1998 |
| WO | WO 9914648 | 3/1999 |
| WO | WO 0012037 | 3/2000 |
| WO | WO 0186369 | 11/2001 |
| WO | WO 0201310 | 1/2002 |
| WO | WO 03053293 A2 | 7/2003 |
| WO | WO 03053293 A3 | 7/2003 |
| WO | WO 03053294 A2 | 7/2003 |
| WO | WO 03053294 A3 | 7/2003 |

* cited by examiner

FOOTSWITCH ASSEMBLY WITH POSITION MEMORY

FIELD

The present invention pertains to footswitch assemblies; more particularly the present invention pertains to footswitch assemblies used to control the operation of a piece of equipment.

BACKGROUND

Footswitch assemblies such as those used to provide a control input are often found with sophisticated pieces of medical equipment. Such footswitch assemblies give a medical professional the ability to use his/her hands when positioning and manipulating instruments while conducting a medical procedure on a patient. Such footswitch assemblies are used to control surgical parameters using small foot movements.

Typical footswitch assemblies have a base housing portion and a movable treadle pedal pivotably mounted to the base housing portion. In some footswitches, the base housing portion also includes side wings which are located on either side of the treadle pedal. On and off switches are located on the side wings. Within the base housing portion are typically located the mechanical support for the pivotable mounting of the movable treadable pedal and an array of electrical connections.

The physical inputs into a footswitch assembly by a healthcare professional, particularly a surgeon, are often used to regulate very critical parameters. If these delicate parameters are not properly regulated, disastrous consequences can result.

Users of footswitch assemblies typically become accustomed to the feel of certain footswitches and are able to repeatedly execute successful procedures quickly and efficiently because of the muscle memory associated with the use of footswitches having a generally uniform design. Unfortunately, different sophisticated medical equipment systems use different styles and different types of footswitches. Because of the size, the complexity, the variety and the cost of footswitches, those using footswitches on a regular basis do not have their own customized universal footswitch which can be transported and used to operate a variety of different types of equipment.

Further complicating the problem of the use of footswitches is that users of footswitch assemblies have different sized feet. Specifically, foot sizes vary in both length and width. Not only does the variation in foot sizes require that the footswitch assemblies accommodate the feet of all expected users, but the length of a user's foot also affects the amount of force needed to move the movable treadle pedal of the footswitch assembly with respect to its pivotable mounting. When a user is paired up with a footswitch assembly that has never been previously used by that user, the user must get used to the control "touch and feel" of the footswitch assembly to make the proper control inputs when operating a piece of equipment; for example, a piece of equipment used to perform surgical procedures.

If the footswitch assembly is being used to control a piece of equipment to perform a delicate medical procedure such as cataract or vitreoretinal surgery, the beginning of such a delicate surgical procedure is not the most propitious time for the vitreoretinal surgeon to practice becoming accustomed to the control touch and feel of a new footswitch assembly.

Accordingly, there remains a need in the art for a footswitch assembly with position memory which automatically adjusts to the size of an operator's foot and the desired control touch and feel of the user.

SUMMARY

The disclosed footswitch with position memory of the present invention automatically adjusts to the size of an operator's foot and the desired control touch and feel of the user.

Included within the base housing portion of the footswitch assembly with position memory of the present invention are three servo motors. Each servo motor receives input from a position memory device to enable two of the servo motors to adjust both the length and width of the footswitch assembly to the size of the operator's foot and a third servo motor to set the control touch and feel of treadle pedal movement to the operator's preference.

The first servo motor is positioned under the side wings in the base housing portion of the footswitch assembly. The mechanism attached to the first servo motor moves the side switches closer to or away from the centerline of the footswitch assembly to accommodate either a wide foot, a narrow foot or something in-between.

The second servo motor is positioned near the back of the footswitch assembly where the heel cup is typically located. Operation of the second servo motor moves the heel cup substantially parallel to the centerline of the footswitch assembly to accommodate either a long foot or a short foot or something in-between.

The third servo motor is connected to a mechanism attached to the spring bias which governs the force required to move the pivoting treadle pedal of the footswitch assembly through its range of motion.

BRIEF DESCRIPTION OF THE DRAWING FIGURES

A better understanding of the footswitch assembly with position memory of the present invention made be had by reference to the following designated drawing figures when read in conjunction with the Description of the Embodiments.

DESCRIPTION OF THE EMBODIMENTS

The footswitch assembly with position memory 10 of the present invention is disclosed herein according to its use with an ophthalmic surgical system. Those of ordinary skill in the art will understand that the footswitch assembly with position memory 10 of the present invention may be used with other types of medical equipment such as may be used by dentists or veterinarians. Still others will understand that the footswitch assembly of the present invention may also be used with non-medical equipment whose operation requires the use of a footswitch assembly with position memory.

Figure 1:
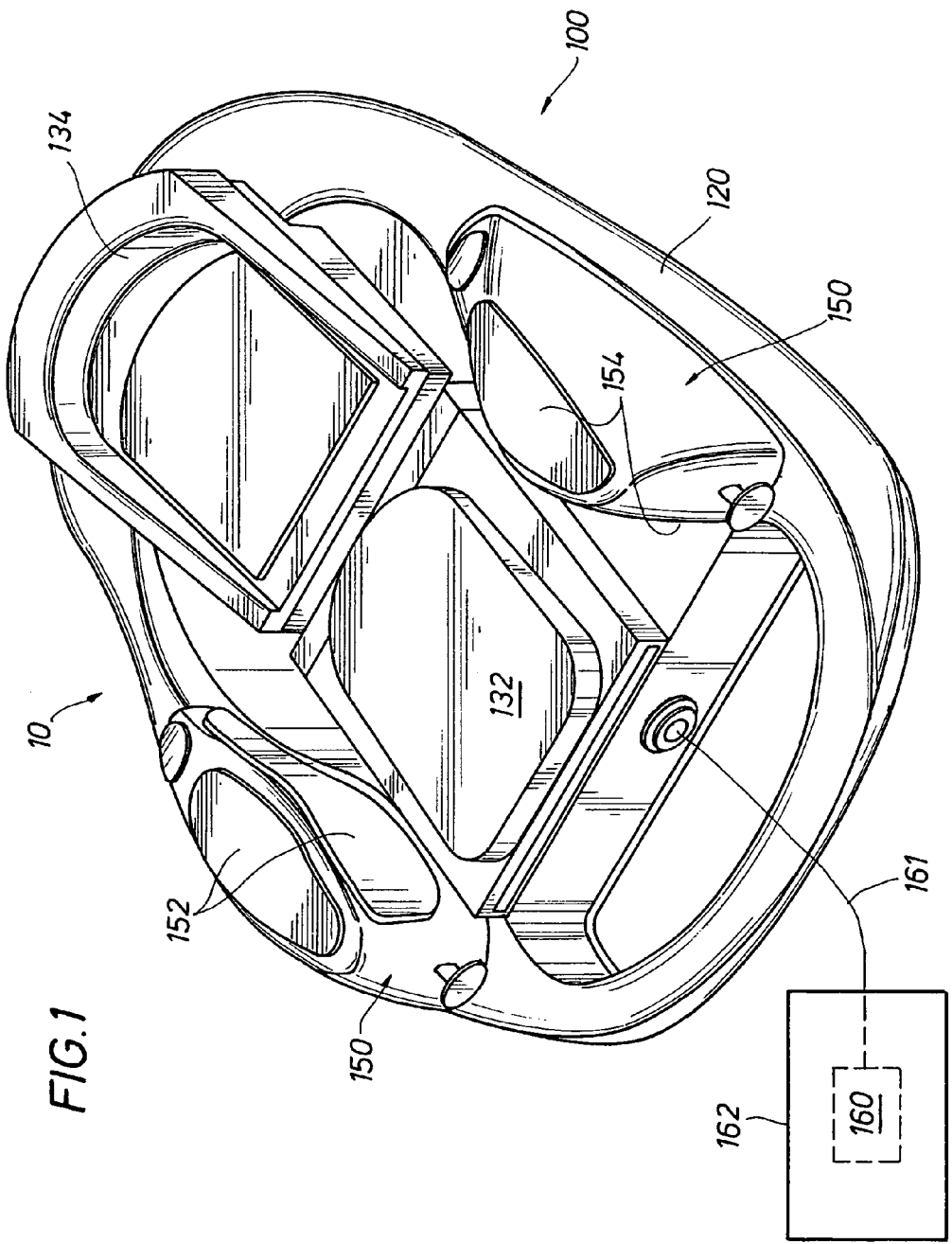
FIG. 1 is a perspective view of a typical footswitch assembly.

As best seen in FIG. 1, a typical footswitch assembly 100 has a base housing portion 120 and a movable treadle pedal assembly 130. The base housing portion 120 provides support for the footswitch assembly 100 and an internal pivot (not shown) about which the pivotable movement of the treadle pedal assembly 130 is. enabled. At the back of the treadle pedal assembly 130 is a heel cup 134 in which the user places the heel of his/her foot. At the front of the treadle pedal assembly 130 is a treadle pedal 132. Treadle pedal 132 and heel cup 134 are preferably integrally mounted. Treadle pedal assembly 130 may be used to proportionally control a surgical function. At the front of footswitch assembly 100 extending upwardly from the base housing portion 120 and positioned on either side of the treadle pedal assembly 130 are side wing assemblies 150. Located within the side wing assemblies 150 are side switches 152, 154. Side switches 152, 154 are typically on/off switches that may be used to start or stop a particular surgical function.

Because the foot size and the foot strength of all users of a footswitch assembly 100 are not the same, there is a need to tailor the physical size of the footswitch assembly 100 to match the size of an operator's foot. Additionally, there is a need to tailor the bias force or control "touch and feel" associated with the movements of the treadle pedal assembly 130 to the force that can be applied by a user's foot.

Figure 2:
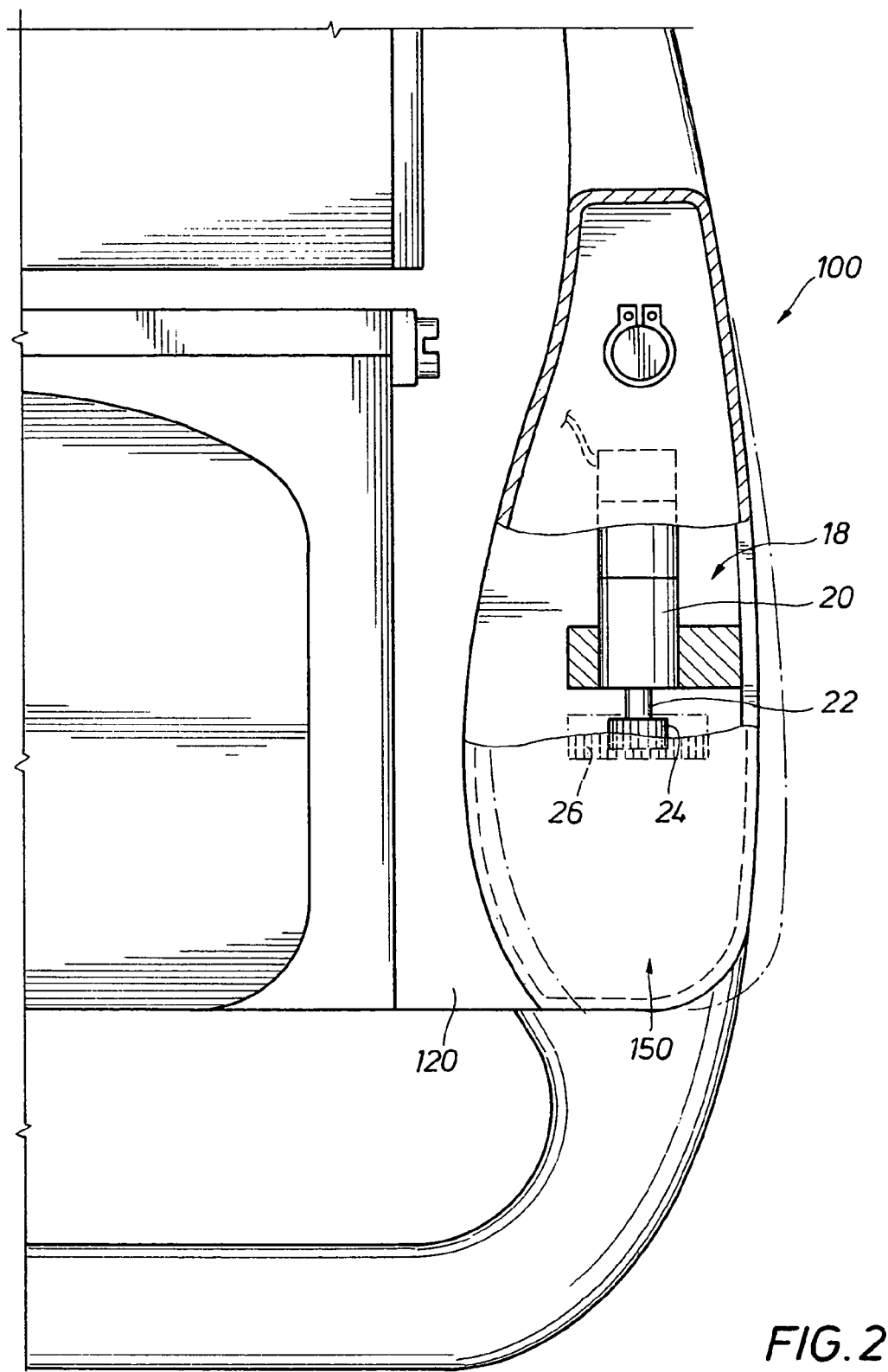
FIG. 2 is a plan view of that portion of the base of the footswitch assembly of the present invention which controls the position of the side switches to accommodate feet of different widths.

In the footswitch assembly with position memory 10 of the present invention and as shown in FIG. 2, the first movement mechanism 18 enabling the adjustment for the width of a user's foot relates to the position of the side wing assemblies 150. A positionable DC servo motor 20 is mounted within the base housing portion 120 of the footswitch assembly 100. Extending from the servo motor 20 is a shaft 22 on which is mounted a pinion gear 24. The pinion gear 24 engages a stationary gear rack 26. Because the side wing assembly 150 is pivotably 152 mounted to the base housing portion 120, the turning of the pinion gear 24 against the stationary gear rack 26 will cause the side wing assembly 150 to move about its pivotable 152 mounting. This movement will cause the side switch assembly 150 to move closer to or farther away from the center line of the footswitch assembly 100 in a substantially perpendicular manner. In the preferred embodiment, two pivotably mounted side wing assemblies 150, mounted on either side of the center line of the base housing portion 120, will be constructed and arranged to include a positionable DC servo motor 20, a pinion gear 24 and a stationary gear rack 26 located thereunder.

Figure 3:
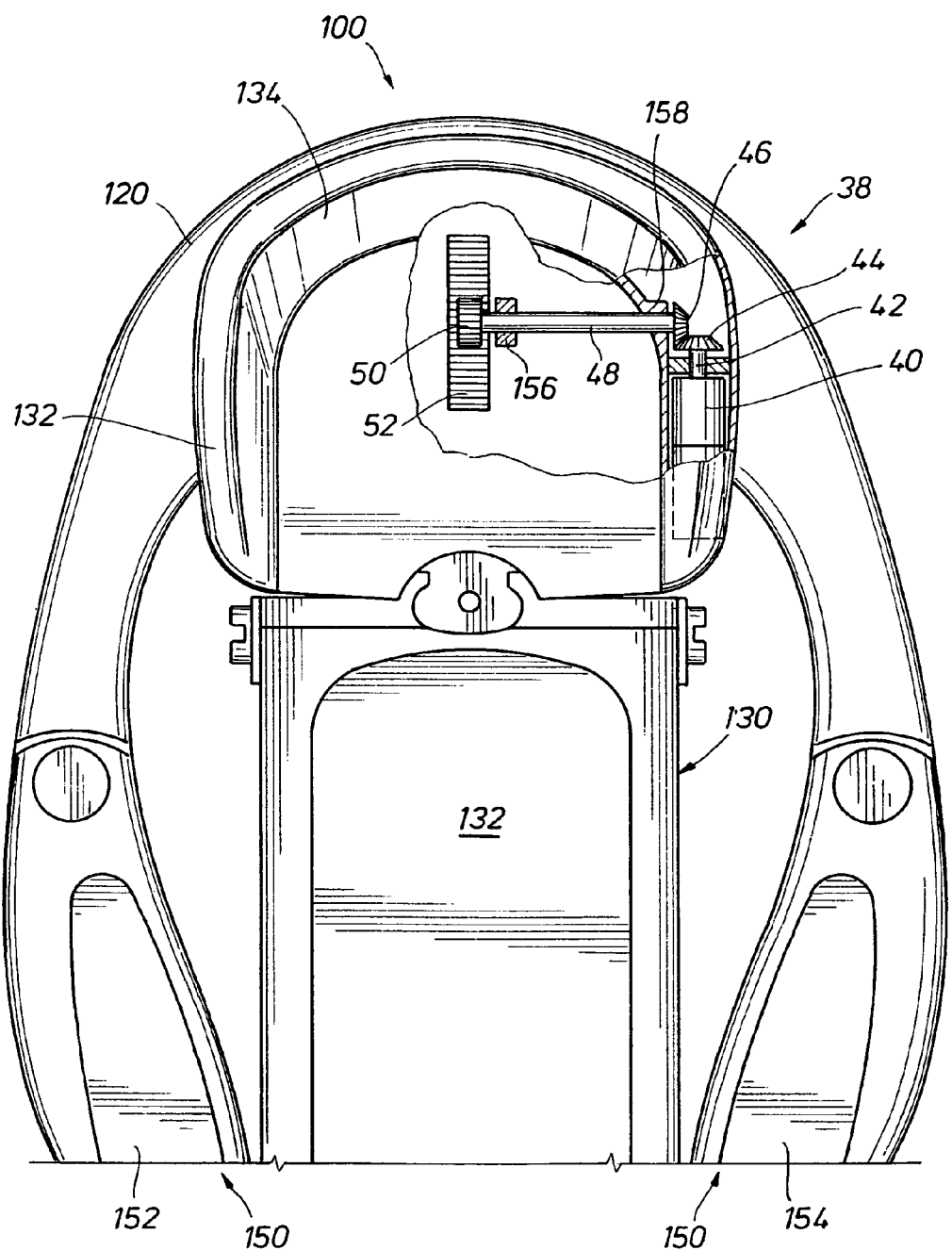
FIG. 3 is a plan view of that portion of the base of the footswitch assembly of the present invention which controls the position of the heel cup to accommodate feet of different lengths.

As shown in FIG. 3, the second movement mechanism 38 enabling the adjustment for the length of a user's foot is constructed and arranged under the heel cup 134 at the back end of the treadle pedal assembly 130. Within the side of the heel cup 134 is a positionable DC servo motor 40. Extending from the DC servo motor 40 is a shaft 42 on which is mounted a first bevel gear 44. A second bevel gear 46 engages the first bevel gear 44. Attached to the second bevel gear 46 is a shaft 48 having a pinion gear 50 mounted on the opposite end from the second bevel gear 46. The pinion gear 50 engages a stationary rack 52. Thus when the positionable DC servo motor 40 turns, the rotary motion turns the bevel gear set 44, 46, which causes the pinion gear 50 to move on the stationary rack 52 in a direction which is substantially parallel to the center line of the base housing portion 120. The user sets the heel cup 134 at the proper position so that the front of the user's foot (not shown) is located near the front of the treadle pedal 132 and the sides of the front of the user's foot are near the side switches 152, 154 on the side wing assemblies 150. One or more bearing supports 156,158 may be used to support the shaft 48.

Figure 4:
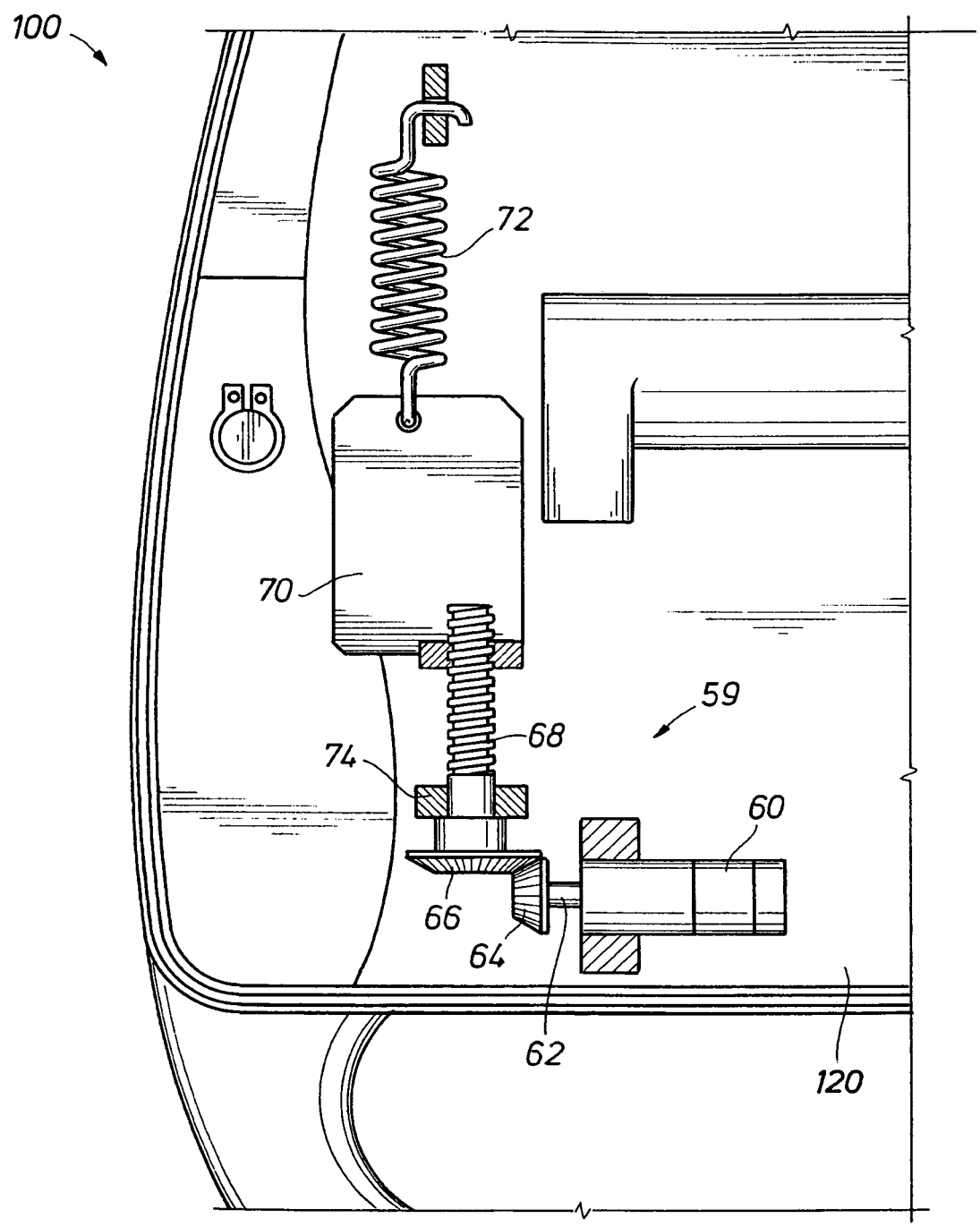
FIG. 4 is a plan view of that portion of the base of the footswitch assembly of the present invention which controls the spring bias on the pivoting treadle pedal.

In FIG. 4, the adjustment for the control touch and feel of the movement of the treadle pedal assembly 130 is shown. Specifically, some users with a desire for a heavy control touch may desire that significant force be associated with treadle pedal assembly 130 movement. Others with a desire for a light control touch may desire a slight force and only desire that just enough bias be used to return the treadle pedal assembly 130 to a neutral position when foot pressure is released. As with the other two adjustment mechanisms shown in FIG. 2 and FIG. 3, a third movement mechanism 59 including a positionable DC servo motor 60 is mounted to the bottom side of base housing portion 120 of the footswitch assembly 100. Extending from the positionable DC servo motor 60 is a shaft 62 on which is mounted a first bevel gear 64. The first bevel gear 64 engages a second bevel gear 66. The second bevel gear 66 is mounted to the end of a lead screw 68. Turning of the lead screw 68 within a threaded connection 73 on a plate 70 causes the plate 70 to move. Attached to the plate 70 is a coil spring 72. Extending the length of the coil spring 72 causes more force to be exerted by the user to move the treadle pedal assembly 130 about its pivot. Shortening of the coil spring 72 causes less force to be exerted by the user to move the treadle pedal assembly 130 about its pivot. At a selected length of the coil spring 72, a predetermined amount of force needed to move the pivotable treadle pedal assembly 130 is enabled. A bearing support 74 may be used to hold the lead screw 68 in position.

A medical professional such as an ophthalmic surgeon may use a computer 162 electrically coupled to footswitch assembly 10 via an interface 161 to define a set of position settings which provide both a comfortable fit and comfortable operation of the footswitch. These position settings are associated with the position of the positionable DC servo motors 20, 40, and 60 which control the sizing and operation of the footswitch assembly 10. Information about the positions of the one or more servo motors 20, 40 and 60 are retained in a computer memory 160 of computer 162 until needed. Computer memory 160 may be located external to footswitch assembly 10 as shown in FIG. 1. Alternatively, computer memory 160 may be located within footswitch assembly 10.

When a medical professional such as an ophthalmic surgeon prepares to perform a surgical operation on a patient, the surgeon enters a code at a remote location such as a control screen of computer 162 to identify himself/herself. The code identifying the user is associated with a set of stored preferred positions for the positionable DC servo motor 20, 40, 60 settings stored in computer memory 160. When a signal from the computer 162 initiates remote movement of the movement mechanisms 18, 38 and 59 within the footswitch assembly 10, electrical energy is applied to the positionable DC servo motors 20, 40, 60. Each positionable DC servo motor 20, 40, 60 then moves to the predetermined setting for the user. The footswitch assembly 100 is thereby customized to size of the user's foot and the desired control touch feel.

While the present invention has been disclosed according to its preferred embodiment, those of ordinary skill in the art will understand that numerous other embodiments have been enabled by the foregoing disclosure. Such other embodiments shall be included with the scope and meaning of the appended claims.

What is claimed is:

1. A footswitch assembly enabling position memory comprising:
   a base housing portion having a center line;
   a pivotably mounted side wing assembly positioned on either side of said base housing portion, said pivotably mounted side wing assembly having a switch mounted therein;
   a movable treadle pedal assembly;
   a heel cup located on said treadle pedal assembly;
   a first movement mechanism constructed and arranged to move said pivotably mounted side wing assemblies substantially perpendicular to said center line of said base housing portion;
   a second movement mechanism constructed and arranged to move said heel cup substantially parallel to said center line of said base housing portion;
   a third movement mechanism constructed and arranged to adjust the amount of force needed to move said movable treadle pedal assembly;
   said first movement mechanism and said second movement mechanism each including a positionable servo motor for enabling a user to place said side wing assemblies and said heel cup in a predetermined position;
   said third movement mechanism including a positionable servo motor for enabling a user to adjust the force needed to move said movable treadle pedal assembly.

2. The footswitch assembly as defined in claim 1 wherein said first movement mechanism includes a pinion gear mounted to said positionable servo motor and a rack mounted to said base housing portion.

3. The footswitch assembly as defined in claim 1 wherein said second movement mechanism includes a pinion gear, a rack, and a set of bevel gears mounted to said positionable servo motor.

4. The footswitch assembly as defined in claim 1 wherein said third movement mechanism includes a set of bevel gears mounted to said positionable servo motor and a lead screw for changing the force exerted by a spring.

5. The footswitch assembly as defined in claim 1 further including a computer memory for enabling changing the position of said first movement mechanism, said second movement mechanism and said third movement mechanism to a predetermined position.

6. A footswitch assembly with position memory, said footswitch assembly with position memory including a base housing, at least one side wing assembly, and a treadle pedal assembly with a heel cup mounted thereon, said footswitch assembly comprising:
   a mounting for the heel cup enabling remote initiation of the movement of the heel cup substantially parallel to the center line of the base housing to a predetermined position;
   a mounting for the at least one side wing assembly enabling remote initiation of the movement of the at least one side wing assembly substantially perpendicular to the center line of the base housing to a predetermined position;
   a mounting for the movable treadle pedal assembly enabling remote initiation of the adjustment of the force required to move the movable treadle pedal assembly to a predetermined amount of force.

7. The footswitch assembly with position memory as defined in claim 6 wherein said mounting for the heel cup includes a positionable servo motor and a gear mechanism to position the heel cup to said predetermined position.

8. The footswitch assembly with position memory as defined in claim 6 wherein said mounting for the at least one side wing assembly includes a positionable servo motor and a gear mechanism to position the at least one side wing assembly to said predetermined position.

9. The footswitch assembly with position memory as defined in claim 6 wherein said mounting for the pivotable treadle pedal assembly includes a positionable servo motor and a gear mechanism to adjust the amount of force to move the treadle pedal assembly to a predetermined amount.

10. The footswitch assembly with position memory as defined in claim 6 further including a computer memory for said remote initiation of said enabling of the movement of the mounting for the heel cup, the movement of the mounting for the side wing assembly, and the adjustment of the force required to move the pivotable treadle pedal assembly.

11. A method for changing the size and variable control input of a footswitch assembly having a treadle pedal assembly with a heel cup, at least one side wing assembly on either side of said treadle pedal assembly, and a bias spring controlling the force required to move said treadle pedal assembly, said method comprising the steps of:
   mounting the heel cup to a gear disposed in a rack, wherein said gear which is movable by a positionable servo motor;
   mounting the at least one side wing assembly to a second gear disposed in a second rack, wherein said second gear is movable by a second positionable servo motor; and
   mounting the bias spring to a lead screw, wherein said lead screw is coupled to a third gear and said third gear is movable by a positionable servo motor.

* * * * *